(12) United States Patent
Stueven et al.

(10) Patent No.: US 8,748,000 B2
(45) Date of Patent: *Jun. 10, 2014

(54) METHOD FOR PRODUCING WATER-ABSORBENT POLYMER PARTICLES WITH A HIGHER PERMEABILITY BY POLYMERIZING DROPLETS OF A MONOMER SOLUTION

(75) Inventors: Uwe Stueven, Bad Soden (DE); Matthias Weismantel, Jossgrund-Oberndorf (DE); Wilfried Heide, Freinsheim (DE); Marco Krüger, Mannheim (DE); Volker Seidl, Mannheim (DE); Stefan Blei, Mannheim (DE); Dennis Loesch, Altrip (DE); Rüdiger Funk, Niedernhausen (DE); Annemarie Hillebrecht, Künzell (DE)

(73) Assignee: BASF SE, Ludwigshafen (DE)

( * ) Notice: Subject to any disclaimer, the term of this patent is extended or adjusted under 35 U.S.C. 154(b) by 489 days.

This patent is subject to a terminal disclaimer.

(21) Appl. No.: 12/306,800

(22) PCT Filed: Jul. 12, 2007

(86) PCT No.: PCT/EP2007/057141
§ 371 (c)(1),
(2), (4) Date: Dec. 29, 2008

(87) PCT Pub. No.: WO2008/009612
PCT Pub. Date: Jan. 24, 2008

(65) Prior Publication Data
US 2009/0192035 A1 Jul. 30, 2009

(30) Foreign Application Priority Data
Jul. 19, 2006 (EP) .................................. 06117487

(51) Int. Cl.
*B32B 5/16* (2006.01)
*B32B 9/00* (2006.01)
*B32B 15/02* (2006.01)

(52) U.S. Cl.
USPC ................ 428/402; 428/402.24; 526/317.1; 604/367; 604/372; 252/194

(58) Field of Classification Search
USPC ................ 526/317.1; 604/367, 372
See application file for complete search history.

(56) References Cited

U.S. PATENT DOCUMENTS

| | | | | |
|---|---|---|---|---|
| 4,418,163 A * | 11/1983 | Murakami et al. | ............ | 523/205 |
| 4,997,867 A * | 3/1991 | Jederstrom et al. | ............ | 524/47 |
| 5,269,980 A | 12/1993 | Levendis et al. | | |
| 5,973,042 A * | 10/1999 | Yoshinaga et al. | ............ | 524/192 |
| 6,174,952 B1 * | 1/2001 | Hekal et al. | ............ | 524/503 |
| 6,277,932 B1 * | 8/2001 | Whitley et al. | ............ | 526/88 |
| 6,756,437 B1 * | 6/2004 | Xue et al. | ............ | 524/401 |
| 8,124,229 B2 * | 2/2012 | Stueven et al. | ............ | 428/402 |
| 2001/0002386 A1 * | 5/2001 | Steele et al. | ............ | 502/401 |
| 2002/0146386 A1 * | 10/2002 | Simon et al. | ............ | 424/78.31 |
| 2005/0119424 A1 * | 6/2005 | Ishii et al. | ............ | 526/88 |
| 2005/0245684 A1 | 11/2005 | Daniel et al. | | |
| 2006/0178071 A1 * | 8/2006 | Schmidt et al. | ............ | 442/417 |
| 2006/0217580 A1 | 9/2006 | Kuechler et al. | | |
| 2006/0252899 A1 * | 11/2006 | Himori et al. | ............ | 526/317.1 |
| 2007/0100115 A1 | 5/2007 | Schmid et al. | | |
| 2007/0244280 A1 | 10/2007 | Losch et al. | | |
| 2007/0293617 A1 | 12/2007 | Riegel et al. | | |
| 2008/0045624 A1 | 2/2008 | Losch et al. | | |
| 2008/0045625 A1 | 2/2008 | Losch et al. | | |
| 2008/0125533 A1 | 5/2008 | Riegel et al. | | |
| 2008/0188821 A1 | 8/2008 | Losch et al. | | |
| 2008/0194778 A1 | 8/2008 | Losch et al. | | |
| 2009/0036855 A1 * | 2/2009 | Wada et al. | ............ | 604/372 |

FOREIGN PATENT DOCUMENTS

| | | |
|---|---|---|
| DE | 102 39 074 | 3/2004 |
| DE | 103 14 466 | 10/2004 |
| DE | 103 40 253 | 3/2005 |
| DE | 10 2004 024 437 | 12/2005 |
| DE | 10 2004 042 946 | 3/2006 |
| DE | 10 2004 042 948 | 3/2006 |
| DE | 10 2004 042 955 | 3/2006 |
| DE | 10 2004 057 868 | 6/2006 |
| DE | 10 2005 002 412 | 7/2006 |
| DE | 10 2005 019 398 | 10/2006 |
| EP | 0 348 180 | 12/1989 |
| EP | 1 029 886 A2 | 8/2000 |
| EP | 1 424 346 | 6/2004 |
| WO | WO-96/40427 | 12/1996 |
| WO | WO-2006/042704 | 4/2006 |

OTHER PUBLICATIONS

Ferric phosphate_Hawley's condensed Chemical Dictionary, 14th Edition, 2002.*
Buchholz et al., *Modern Superabsorbent Polymer Technology*, Wiley-VCH, pp. 71-103 (1998).
Deutsche Anmeldung 10 2006 001 596.7.
International Search Report in PCT/EP2007/057141 dated Nov. 30, 2007.

* cited by examiner

*Primary Examiner* — Irina Krylova
(74) *Attorney, Agent, or Firm* — Marshall, Gerstein & Borun LLP

(57) ABSTRACT

A process for preparing water-absorbing polymer beads with high permeability by polymerizing droplets of a monomer solution in a gas phase surrounding the droplets, wherein a water-insoluble inorganic salt is suspended in the monomer solution and the polymer beads have a mean diameter of at least 150 μm.

6 Claims, No Drawings

METHOD FOR PRODUCING WATER-ABSORBENT POLYMER PARTICLES WITH A HIGHER PERMEABILITY BY POLYMERIZING DROPLETS OF A MONOMER SOLUTION

CROSS-REFERENCE TO RELATED APPLICATIONS

This is the U.S. national phase of International Application No. PCT/EP2007/057141, filed Jul. 12, 2007, which claims the benefit of European Patent Application No. 06117487.6, filed Jul. 19, 2006.

The present invention relates to a process for preparing water-absorbing polymer beads with high permeability by polymerizing droplets of a monomer solution in a gas phase surrounding the droplets, wherein a water-insoluble inorganic salt is suspended in the monomer solution and the polymer beads have a mean diameter of at least 150 µm.

The preparation of water-absorbing polymer beads is described in the monograph "Modern Superabsorbent Polymer Technology", F. L. Buehholz and A T. Graham, Wiley-VCH, 1998, pages 71 to 103.

Being products which absorb aqueous solutions, water-absorbing polymers are used to produce diapers, tampons, sanitary napkins and other hygiene articles, but also as water-retaining agents in market gardening.

The properties of the water-absorbing polymers can be adjusted via the degree of crosslinking. With increasing crosslinking, the gel strength rises and the absorption capacity falls. This means that the centrifuge retention capacity (CRC) decreases with increasing absorbency under load (AUL) (at very high degrees of crosslinking, the absorbency under load also decreases again).

To improve the use properties, for example saline flow conductivity (SFC) in the swollen gel bed in the diaper and absorbency under load (AUL), water-absorbing polymer beads are generally postcrosslinked. This increases only the degree of crosslinking of the bead surface, which allows absorbency under load (AUL) and centrifuge retention capacity (CRC) to be decoupled at least partly. This postcrosslinking can be performed in aqueous gel phase. However, preference is given to coating ground and screened polymer beads (base polymer) with a postcrosslinker on the surface, thermally postcrosslinking them and drying them. Crosslinkers suitable for this purpose are compounds which comprise at least two groups which can form covalent bonds with the carboxylate groups of the hydrophilic polymer.

Spray polymerization combines the process steps of polymerization and drying. In addition, the particle size is set within certain limits by suitable process control.

The preparation of water-absorbing polymer beads by polymerizing droplets of a monomer solution is described, for example, in EP-A 0 348 180, WO 96/40427, U.S. Pat. No. 5,269,980, DE-A 103 14 466, DE-A 103 40 253 and DE-A 10 2004 024 437, and also the prior German applications 10 2005 002 412.2 and 10 2006 001 596.7.

DE-A 10 2004 042 946, DE-A 10 2004 042 948 and DE-A 10 2004 042 955, and also the prior German application having the reference number 10 2005 019 398.6, describe the preparation of thickeners by spray polymerization.

It was an object of the present invention to provide a process for preparing water-absorbing polymer beads with high permeability, i.e. high saline flow conductivity through the swollen gel bed.

The object is achieved by a process for preparing water-absorbing polymer 10 beads by polymerizing droplets of a monomer solution comprising a) at least one water-soluble ethylenically unsaturated monomer,
b) at least one crosslinker,
c) at least one initiator,
d) water, in a gas phase surrounding the droplets, wherein a water-insoluble inorganic salt is suspended in the monomer solution and the polymer beads have a mean diameter of at least 150 µm.

The water-absorbing polymer beads obtainable by the process according to the invention have a permeability (SFC) of typically at least $5 \times 10^{-7}$ cm$^3$s/g, preferably at least $15 \times 10^{-7}$ cm$^3$s/g, preferably at least $35 \times 10^{-7}$ cm$^3$s/g, more preferably at least $50 \times 10^{-7}$ cm$^3$s/g, most preferably at least $120 \times 10^{-7}$ cm$^3$s/g. The permeability (SFC) of the water-absorbing polymer beads is typically less than $500 \times 10^{-7}$ cm$^3$s/g.

The water-absorbing polymer beads obtainable by the process according to the invention have a centrifuge retention capacity (CRC) of typically at least 10 g/g, preferably at least 15 g/g, preferentially at least 20 gig, more preferably at least 25 g/g, most preferably at least 30 gig. The centrifuge retention capacity (CRC) of the water-absorbing polymer beads is typically less than 50 g/g.

The water-insoluble inorganic salts can be added to the monomer solution as a powder or as a dispersion in a suitable dispersion medium, for example water.

Water-insoluble means a solubility of less than 2 g, preferably of less than 0.1 g, more preferably of less than 0.01 g, in 100 ml of water at 25° C.

The water-insoluble inorganic salts have a mean particle size of typically less than 400 µm, preferably less than 100 µm, preferentially less than 50 µm, more preferably of less than 10 µm; very particular preference is given to the particle size range of from 2 to 7 µm.

Suitable water-insoluble inorganic salts are, for example, calcium sulfate and calcium phosphate.

Preference is given to using calcium phosphate.

The amount of water-insoluble inorganic salt which is added to the monomer solution is typically at least 0.1% by weight, preferably at least 0.5% by weight, preferentially at least 1% by weight, more preferably at least 2% by weight, most preferably at least 5% by weight, based in each case on monomer a). Excessively high amounts are difficult to disperse, i.e. a content of more than 25% by weight, based again on the monomer a), is therefore not appropriate.

The mean diameter of the polymer beads is preferably at least 200 µm, more preferably from 250 to 600 µm, very particularly from 300 to 500 µm, the bead diameter being determinable by light scattering and meaning the volume-average mean diameter. 90% of the polymer beads have a diameter of preferably from 100 to 800 µm, more preferably from 150 to 700 pm, most preferably from 200 to 600 pm.

The oxygen content of the gas phase is preferably from 0.001 to 0.15% by volume, more preferably from 0.002 to 0.1% by volume, most preferably from 0.005 to 0.05% by volume.

In addition to oxygen, the gas phase comprises preferably only inert gases, i.e. gases which do not intervene in the polymerization under reaction conditions, for example nitrogen and/or water vapor.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 50 g/100 g of water, and preferably have at least one acid group each.

The concentration of the monomers a) in the monomer solution is typically from 2 to 80% by weight, preferably from 5 to 70% by weight, more preferably from 10 to 60% by weight.

Suitable monomers a) are, for example, ethylenically unsaturated carboxylic acids such as acrylic acid, methacrylic acid, maleic acid, fumaric acid and itaconic acid. Particularly preferred monomers are acrylic acid and methacrylic acid. Very particular preference is given to acrylic acid.

The preferred monomers a) have at least one acid group, the acid groups preferably having been at least partly neutralized.

The proportion of acrylic acid and/or salts thereof in the total amount of monomers a) is preferably at least 50 mol %, more preferably at least 90 mol % and most preferably at least 95 mol %.

The acid groups of the monomers a) have typically been neutralized partly, preferably to an extent of from 25 to 85 mol %, preferentially to an extent of from 50 to 80 mol %, more preferably to an extent of from 60 to 75 mol %, for which the customary neutralizing agents can be used, preferably alkali metal hydroxides, alkali metal oxides, alkali metal carbonates or alkali metal hydrogencarbonates, and mixtures thereof. Instead of alkali metal salts, it is also possible to use ammonium salts. Sodium and potassium are particularly preferred alkali metals, but very particular preference is given to sodium hydroxide, sodium carbonate or sodium hydrogencarbonate and mixtures thereof. Typically, the neutralization is achieved by mixing in the neutralizing agent as an aqueous solution, as a melt or else preferably as a solid. For example, sodium hydroxide may be present with a water content significantly below 50% by weight as a waxy mass with a melting point above 23° C. In this case, metering as piece material or a melt at elevated temperature is possible.

The monomers a), especially acrylic acid, comprise preferably up to 0.025% by weight of a hydroquinone monoether. Preferred hydroquinone monoethers are hydroquinone monomethyl ether (MEHQ) and/or tocopherols.

Tocopherol is understood to mean compounds of the following formula

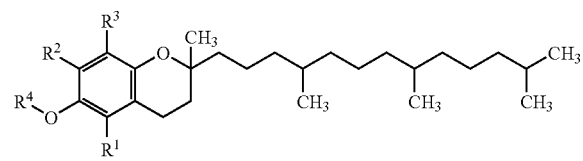

where $R^1$ is hydrogen or methyl, $R^2$ is hydrogen or methyl, $R^3$ is hydrogen or methyl, and $R^4$ is hydrogen or an acyl radical having from 1 to 20 carbon atoms.

Preferred radicals for $R^4$ are acetyl, ascorbyl, succinyl, nicotinyl and other physiologically compatible carboxylic acids. The carboxylic acids may be mono-, di- or tricarboxylic acids.

Preference is given to alpha-tocopherol where $R^1=R^2=R^3=$methyl, in particular racemic alpha-tocopherol. $R^1$ is more preferably hydrogen or acetyl. RRR-alpha-tocopherol is especially preferred.

The monomer solution comprises preferably at most 130 ppm by weight, more preferably at most 70 ppm by weight, preferably at least 10 ppm by weight, more preferably at least 30 ppm by weight, in particular around 50 ppm by weight, of hydroquinone monoether, based In each case on acrylic acid, acrylic acid salts also being considered as acrylic acid. For example, the monomer solution can be prepared by using acrylic acid having an appropriate content of hydroquinone monoether.

The crosslinkers b) are compounds having at least two free-radically polymerizable groups which can be polymerized by a free-radical mechanism into the polymer network. Suitable crosslinkers b) are, for example, ethylene glycol dimethacrylate, diethylene glycol diacrylate, allyl methacrylate, trimethylolpropane triacrylate, triallylamine, tetraallyloxyethane, as described in EP-A-0 530 438, di- and triacrylates, as described in EP-A-0 547 847, EP-A-0 559 476, EP-A-0 632 068, WO 93/21237, WO 03/104299, WO 031104300, WO 03/104301 and in DE-A-103 31 450, mixed acrylates which, as well as acrylate groups, comprise further ethylenically unsaturated groups, as described in DE-A-103 314 56 and DE-A 103 55 401, or crosslinker mixtures, as described, for example, in DE-A-195 43 368, DE-A-196 46 484, WO 90/15830 and WO 02/32962.

Suitable crosslinkers b) are in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate or ethylene glycol dimethacrylate, and also trimethyloipropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and vinyiphosphonic acid derivatives, as described, for example, in EP-A-0 343 427. Further suitable crosslinkers b) are pentaerythritol diallyl ether, pentaerythritol trialtyf ether and pentaerythritol tetraally/ether, polyethylene glycol diallyl ether, ethylene glycol diallyl ether, glycerol diallyl ether and glycerol Wallyl ether, polyallyl ethers based on sorbitol, and ethoxylated variants thereof. In the process according to the invention, it is possible to use di(meth)acrylates of polyethylene glycols, the polyethylene glycol used having a molecular weight between 300 and 1000.

However, particularly advantageous crosslinkers b) are di- and triacrylates of 3- to 15-tuply ethoxylated glycerol, of 3- to 15-tuply ethoxylated trimethylolpropane, of 3- to 15-tuply ethoxylated trimethylolethane, in particular di- and triacrylates of 2- to 6-tuply ethoxylated glycerol or of 2- to 6-tuply ethoxylated trimethylolpropane, of 3-tuply propoxylated glycerol or of 3-tuply propoxylated trimethylolpropane, and also of 3-tuply mixed ethoxylated or propoxylated glycerol or of 3-tuply mixed ethoxylated or propoxylated trimethylolpropane, of 15-tuply ethoxylated glycerol or of 15-tuply ethoxylated trimethylolpropane, and also of 40-tuply ethoxylated glycerol, of 40-tuply ethoxylated trimethylolethane or of 40-tuply ethoxylated trimethylolpropane.

Very particularly preferred crosslinkers b) are the polyethoxylated and/or-propoxylated glycerols which have been esterified with acrylic acid or methacrylic acid to give di- or triacrylates, as described, for example in WO 03/104301. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol. These feature particularly low residual contents (typically below 10 ppm by weight) in the water-absorbing polymer, and the aqueous extracts of the water-absorbing polymers thus produced have an almost unchanged surface tension (typically at least 0.068 N/m) in comparison to water at the same temperature.

The monomer solution comprises typically at least 0.2% by weight, preferably at least 0.4% by weight, preferentially at least 0.6% by weight, more preferably at least 0.8% by weight and most preferably at least 1.5% by weight, of crosslinker b), based in each case on monomer a).

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane] dihydrochioride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxy-methylsulfinie acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one and mixtures thereof.

The initiators are used in customary amounts, for example in amounts of from 0.001 to 5% by weight, preferably from 0.01 to 1% by weight, based on the monomers a).

For optimal action, the preferred polymerization inhibitors require dissolved oxygen. Therefore, the monomer solution can be freed of dissolved oxygen before the polymerization by inertization, i.e. flowing through with an inert gas, preferably nitrogen. The oxygen content of the monomer solution is preferably lowered before the polymerization to less than 1 ppm by weight, more preferably to less than 0.5 ppm by weight.

The polymerization inhibitors can also be removed by absorption, for example on activated carbon.

For the polymerization in the gas phase, the monomer solution can be dropletized.

The polymerization in the monomer solution droplets preferably takes place in homogeneous phase, not taking account of inhoniogeneities caused by the suspended inorganic salt. This means that the monomer solution is homogeneous and that the monomer solution remains homogeneous even during the polymerization. The polymer may swell during the polymerization but not precipitate out and form a second phase in the droplet. Otherwise, several polymer nuclei would form in each droplet and form agglomerates of very small primary particles during the drying. The aim of the process according to the invention is the production of one primary particle each per droplet. The monomers a) and the crosslinkers b) are therefore to be selected such that the resulting polymer is swellable in the aqueous phase of the droplet.

The process according to the invention is preferably performed in the absence of hydrophobic inert solvents. Hydrophobic inert solvents are virtually all water-immiscible liquids which do not intervene in the polymerization, i.e. comprise no polymerizable groups. Water-immiscible means that the solubility of the hydrophobic solvents in water is less than 5 g/100 g, preferably less than 1 g/100 g, more preferably less than 0.5 g/100 g.

The dropletization involves metering a monomer solution into the gas phase to form droplets. The dropletization of the monomer solution can be carried out, for example, by means of a dropletizer plate.

A dropletizer plate is a plate having at least one bore, the liquid entering the bore from the top. The dropletizer plate or the liquid can be oscillated, which generates a chain of ideally monadisperse droplets at each bore on the underside of the dropletizer plate.

The number and size of the bores is selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The dropletizer is operated in the flow range of laminar jet decomposition, i.e. the Reynolds number based on the throughput per bore and the bore diameter is preferably less than 2000, preferentially less than 1000, more preferably less than 500 and most preferably less than 100. The pressure drop over the bore is preferably less than 2.5 bar, more preferably less than 1.5 bar and most preferably less than 1 bar.

The dropletizer plate has typically at least one bore, preferably at least 10, more preferably at least 50 and typically up to 10 000 bores, preferably up to 5000, more preferably up to 1000 bores, the bores typically being distributed uniformly over the dropletizer plate, preferably in so-called triangular pitch, i.e. three bores in each case form the corners of an equilateral triangle.

The diameter of the bores is adjusted to the desired droplet size.

It may be advantageous to place the dropletizer plate onto a carrier plate, the carrier plate likewise having bores. In this case, the bores of the carrier plate have a greater diameter than the bores of the dropletizer plate and are arranged such that below each bore of the dropletizer plate is disposed a concentric bore of the carrier plate. This arrangement enables a rapid exchange of the dropletizer plate, for example in order to generate droplets of another size.

However, the dropletization can also be carried out by means of pneumatic drawing dies, rotation, cutting of a jet or rapidly actuable microvalve dies.

In a pneumatic drawing die, a liquid jet together with a gas stream is accelerated through a hole diaphragm. The gas rate can be used to influence the diameter of the liquid jet and hence the droplet diameter.

In the case of dropletization by rotation, the liquid passes through the orifices of a rotating disk. As a result of the centrifugal force acting on the liquid, droplets of defined size are torn off. Rotary dropletization is described, for example, in DE-A 4308842 and U.S. Pat. No. 6,338,438.

The emerging liquid jet can also be cut into defined segments by means of a rotating blade. Each segment then forms a droplet.

In the case of use of microvalve dies, droplets with defined liquid volume are generated directly.

The gas phase preferably flows as carrier gas through the reaction chamber, The carrier gas can be conducted through the reaction chamber in cocurrent or in countercurrent to the free-falling droplets of the monomer solution, preferably in cocurrent. After one pass, the carrier gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The polymerization is preferably carried out in a laminar gas flow. A laminar gas flow is a gas flow in which the individual layers of the flow do not mix but rather move in parallel. A measure of the flow conditions is the Reynolds number (Re). Below a critical Reynolds number ($Re_{crit}$) of 2300, the gas flow is laminar. The Reynolds number of the laminar gas flow is preferably less than 2000, more preferably less than 1500 and most preferably less than 1000. The lower limiting case of the laminar inert gas flow is a standing inert gas atmosphere (Re=0), i.e. inert gas is not fed in continuously.

The gas velocity is preferably adjusted such that the flow in the reactor is directed, for example no convection currents opposed to the general flow direction are present, and is, for example, from 0.1 to 2 m/s, preferably from 0.5 to 1.8 m/s, more preferably from 1 to 1.5 m/s.

The carrier gas is appropriately preheated to the reaction temperature upstream of the reactor.

The reaction temperature in the thermally induced polymerization is preferably from 70 to 250X, more preferably from 100 to 220° C. and most preferably from 120 to 200° C.

The reaction can be carried out under elevated pressure or under reduced pressure; preference is given to a reduced pressure of up to 100 mbar relative to ambient pressure.

The reaction offgas, i.e. the carrier gas leaving the reaction chamber, may, for example, be cooled in a heat exchanger. This condenses water and unconverted monomer a). The reaction offgas can then be reheated at least partly and recycled into the reactor as cycle gas. A portion of the reaction offgas can be discharged and replaced by fresh carrier gas, in which case water and unconverted monomers a) present in the reaction offgas can be removed and recycled.

Particular preference is given to a thermally integrated system, i.e. a portion of the waste heat in the cooling of the offgas is used to heat the cycle gas.

The reactors can be trace-heated, in this case, the trace heating is adjusted such that the wall temperature is at least 5° C. above the internal reactor temperature and condensation on the reactor walls is reliably prevented.

The reaction product can be withdrawn from the reactor in a customary manner, for example at the bottom by means of a conveying screw, and, if appropriate, dried down to the desired residual moisture content and to the desired residual monomer content.

Of course, the polymer beads can subsequently be postcrosslinked for further improvement of the properties.

Suitable postcrosslinkers are compounds which comprise at least two groups which can form covalent bonds with the carboxylate groups of the hydrogel. Suitable compounds are, for example, alkoxysilyl compounds, polyaziridines, polyamines, polyamidoamines, di- or polyglycidyl compounds, as described in EP-A-0 083 022, EP-A-0 543 303 and EP-A-0 937 736, di- or polyfunctional alcohols as described in DE-C-33 14 019, DE-C-35 23 617 and EP-A-0 450 922, or β-hydroxyalkylamides, as described in DE-A-102 04 938 and U.S. Pat. No. 6,239,230.

In addition, DE-A-40 20 780 describes cyclic carbonates, DE-A-198 07 502 describes 2-oxazolidone and its derivatives such as 2-hydroxyethy1-2-oxazolidone, DE-A198 07 992 describes Ws- and poly-2-oxazolidinones, DE-A-198 54 573 describes 2-oxotetrahydro-1,3-oxazine and its derivatives, DE-A-198 54 574 describes N-acy1-2-oxazolidones, DE-A-102 04 937 describes cyclic ureas, DE-A-103 34 584 describes bicyclic amide acetals, EP-A-1 199 327 describes oxetanes and cyclic ureas, and WO 03/031482 describes morpholine-2,3-dione and its derivatives, as suitable postcrosslinkers.

The process according to the invention enables the preparation of water-absorbing polymer beads having a high permeability (SFC) and a high centrifuge retention capacity (CRC). For this combination of properties, an additional postcrosslinking step has to date been absolutely necessary.

The present invention further provides water-absorbing polymer beads which are obtainable by the process according to the invention.

The inventive water-absorbing polymer beads have a content of hydrophobic solvent of typically less than 0.005% by weight, preferably less than 0.002% by weight, more preferably less than 0.001 % by weight and most preferably less than 0.0005% by weight. The content of hydrophobic solvent can be determined by gas chromatography, for example by means of the headspace technique.

Polymer beads which have been obtained by reverse suspension polymerization still comprise typically approx. 0.01 % by weight of the hydrophobic solvent used as the reaction medium.

The inventive water-absorbing polymer beads have a surfactant content of typically less than 1% by weight, preferably less than 0.5% by weight, more preferably less than 0.1% by weight and most preferably less than 0.05% by weight.

Polymer beads which have been obtained by reverse suspension polymerization still comprise typically at least 1% by weight of the surfactant used to stabilize the suspension.

The inventive water-absorbing polymer beads are approximately round, i.e. the polymer beads have a mean sphericity of typically at least 0.84, preferably at least 0.86, more preferably at least 0.88 and most preferably at least 0.9. The sphericity (SPHT) is defined as $$SPHT = \frac{4\pi A}{U^2}$$

where A is the cross-sectional area and U is the cross-sectional circumference of the polymer beads. The mean sphericity is the volume-average sphericity.

The mean sphericity can be determined, for example, with the Carnsizer(®) image analysis system (Retsch Technolgy GmbH; Germany):

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter $xc_{min}$. To determine the equivalent diameter xcee, the longest chord diameter for a total of 32 different spatial directions is measured in each case. The equivalent diameter $xc_{min}$ is the shortest of these 32 chord diameters. The equivalent diameter $xc_{min}$ corresponds to the mesh size of a screen that the particle can just pass through. To record the particles, the so-called CCD-zoom camera (CAM-Z) is used. To control the metering channel, a surface coverage fraction of 0.5% is predefined.

Polymer beads with relatively low sphericity are obtained by reverse suspension polymerization when the polymer beads are agglomerated during or after the polymerization.

The water-absorbing polymer beads prepared by customary solution polymerization (gel polymerization) are ground and classified after drying to obtain irregular polymer beads. The mean sphericity of these polymer beads is between approx. 0.72 and approx. 0.78.

The present invention further relates to the use of the crosslinked water-absorbing polymer beads mentioned above in hygiene articles. For example, the hygiene article may be constructed as follows:

(A) an upper liquid-pervious cover
(B) a lower liquid-impervious layer
(C) a core disposed between (A) and (B), comprising from 10 to 100% by weight of the inventive water-absorbing polymer beads from 0 to 90% by weight of hydrophilic fiber material
  preferably from 30 to 100% by weight of the inventive water-absorbing polymer beads, from 0 to 70% by weight of hydrophilic fiber material more preferably from 50 to 100% by weight of the inventive water-absorbing polymer beads, from 0 to 60% by weight of hydrophilic fiber material,
  especially preferably from 70 to 100% by weight of the inventive water-absorbing polymer beads, from 0 to 30% by weight of hydrophilic fiber material,
  and most preferably from 90 to 100% by weight of the inventive water-absorbing polymer beads, from 0 to 10% by weight of hydrophilic fiber material,
(D) if appropriate a tissue layer disposed immediately above and below the core (C) and
(E) if appropriate an absorption layer disposed between (A) and (C).

Hygiene articles are understood to mean, for example, incontinence pads and incontinence briefs for adults or diapers for babies.

The liquid-pervious cover (A) is the layer which is in direct contact with the skin. The material for this consists of customary synthetic or semisynthetic fibers or films of polyester, polyolefins, rayon or natural fibers such as cotton. In the case of nonwoven materials, the fibers should generally be bound by binders such as polyacrylates. Preferred materials are polyester, rayon and blends thereof, polyethylene and polypropylene. Examples of liquid-pervious layers are described in WO 99/57355, EP-A 1 023 883.

The liquid-impervious layer (B) consists generally of a film of polyethylene or polypropylene, In addition to the inventive water-absorbing polymer beads, the core (C) comprises hydrophilic fiber material Hydrophilic is understood to mean that aqueous liquids spread rapidly over the fibers. Usually, the fiber material is cellulose, modified cellulose, rayon, polyester such as polyethylene terephthalate. Particular preference is given to cellulose fibers such as chemical pulp. The fibers generally have a diameter of from 1 to 200 µm, preferably from 10 to 100 µm. In addition, the fibers have a minimum length of 1 mm.

The structure and the shape of diapers is common knowledge and is described, for example, in WO 95/26209 page 66 line 34 to page 69 line 11, DE-A 196 04 601, EP-A 0 316 518 and EP-A 0 202 127. Diapers and other hygiene articles are also described in general terms in WO 00/65084, especially on pages 6 to 15, WO 00/65348, especially on pages 4 to 17, WO 00/35502, especially pages 3 to 9, DE-A 197 37 434 and WO 98/08439. Hygiene articles for feminine hygiene are described in the following references. The inventive water-absorbing polymer beads can be used there. References on feminine hygiene: WO 95/24173; Absorption Article for Controlling Odour, WO 91/11977: Body Fluid Odour Control, EP-A 0 389 023: Absorbent Sanitary Articles, WO 94/25077: Odour Control Material, WO 97/01317: Absorbent Hygienic Article, WO 99118905, EP-A 0 834 297, U.S. Pat. Nos. 5,762,644, 5,895,381, WO 98157609, WO 00/65083, WO 00/69485, WO 00/69484, WO 00/69481, U.S. Pat. No. 6,123,693, EP-A 1 104 666, WO 01/24755, WO 01/00115, EP-A 0 105 373, WO 01/41692, EP-A 1 074 233. Tampons are described in the following documents: WO 98/48753, WO 98/41179, WO 97109022, WO 98/46182, WO 98/46181, WO 01/43679, WO 01/43680, WO 00/61052, EP-A 1 108 408, WO 01/33962, DE-A 100 20 662, WO 01/01910, WO 01/01908, WO 01/01909, WO 01/01906, WO 01/01905, WO 01/24729. Incontinence articles are described in the following documents: Disposable Absorbent Article for Incontinent individuals: EP-A 0 311 344 description pages 3 to 9, Disposable Absorbent Article: EP-A 0 850 623, Absorbent Article: WO 95/26207, Absorbent Article: EP-A 0 894 502, Dry Laid Fibrous Structure: EP-A 0 850 616, WO 98/22063, WO 97/49365, EP-A 0 903 134, EP-A 0 887 060, EP-A 0 887 059, EP-A 0 887 058, EP-A 0 887 057, EP-A 0 887 056, EP-A 0 931 530, WO 99/25284, WO 98/48753. Feminine hygiene articles and incontinence articles are described in the following documents: Catamenial Device: WO 93/22998 description pages 26 to 33, Absorbent Members for Body Fluids: WO 95/26209 description pages 36 to 69, Disposable Absorbent Article: WO 98/20916 description pages 13 to 24, Improved Composite Absorbent Structures: EP-A 0 306 262 description pages 3 to 14, Body Waste Absorbent Article: WO 90/45973. These references are hereby incorporated explicitly into the disclosure of the invention.

In addition to the above-described inventive water-absorbing polymer beads, constructions which comprise the inventive water-absorbing polymer beads or to which they are fixed may be present in the absorbent composition according to the present invention. A suitable construction is any which can accommodate the inventive water-absorbing polymer beads and which can additionally be integrated into the absorption layer. A multitude of such compositions is already known. A construction for the incorporation of the inventive water-absorbing polymer beads may, for example, be a fiber matrix which consists of a cellulose fiber blend (airlaid web, wet laid web) or of synthetic polymer fibers (meitbiown web, spunbonded web), or else of a fiber blend composed of cellulose fibers and synthetic fibers. Possible fiber materials are described in detail in the chapter which follows. The process of an airlaid web is outlined, for example, in the patent application WO 98/28478. In addition, open-pore foams or the like can serve for the incorporation of water-absorbing polymer beads.

Alternatively, such a construction can be formed by fusing two individual layers to form one chamber or, better, a multitude of chambers which comprise the inventive water-absorbing polymer beads. Such a chamber system is outlined in detail in the patent application EP-A 0 615 736 page 7 lines 26 ff.

In this case, at least one of the two layers should be water-pervious. The second layer may be either water-pervious or water-impervious. The layer material used may be tissues or other fabric, closed or open-cell foams, perforated films, elastomers or fabrics made from fiber material. When the absorbent composition consists of a construction of layers, the layer material should have a pore structure whose pore dimensions are small enough to retain the inventive water-absorbing polymer beads. The above examples of the construction of the absorbent composition also include laminates of at least two layers, between which the inventive water-absorbing polymer beads are incorporated and fixed.

Generally, it is possible to fix hydrogel particles within the absorbent core to improve the so-called dry and wet integrity. Dry and wet integrity is understood to mean the capability of incorporating water-absorbing polymer beads into the absorbent composition such that they withstand external forces both in the wet and in the dry state and there are no dislocations or leakage of highly swellable polymer. Forces are understood to mean in particular mechanical stresses, as occur while moving around when wearing, the hygiene article, or else the weight stress on the hygiene article in the case of incontinence in particular. For the fixing, there are a multitude of possibilities which are known to the person skilled in the art. Examples such as fixing by heat treatment, addition of adhesives, thermoplastics, binder materials are noted in the patent application WO 95/26209 page 37 line 36 to page 41 line 14. Said passage is thus part of this invention. Methods for increasing the wet strength are also found in the patent application WO 00/36216.

In addition, the absorbent composition may also consist of a carrier material, for example a polymer film, on which the water-absorbing polymer beads are fixed. The fixing may be undertaker, either on one side or on both sides. The carrier material may be water-pervious or water-impervious.

In above constructions of the absorbent composition, the inventive water-absorbing polymer beads are incorporated with a proportion by weight of from 10 to 100% by weight, preferably from 30 to 100% by weight, more preferably from 50 to 100% by weight, especially preferably from 70 to 100% by weight, and most preferably from 90to 100% by weight, based on the total weight of the construction and of the water-absorbing polymer beads.

The structure of the present inventive absorbent composition is based on various fiber materials, which are used as a fiber network or matrices. The present invention includes both fibers of natural origin (modified or unmodified) and synthetic fibers.

A detailed overview of examples of fibers which can be used in the present invention is given by the patent application WO 95/26209 page 28 line 9 to page 36 line 8. Said passage is thus part of this invention.

Examples of cellulose fibers include cellulose fibers which are customarily used in absorption products, such as fluff pulp and cellulose of the cotton type. The materials (soft- or hardwoods), prosuction processes such as chemical pulp, semichemical pulp, Chemothermomechanical pulp (CTMP) and bleaching processes are not particularly restricted. For example, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON®) or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyesteripolyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. In addition, the addition of thermoplastic fibers means that there is an increase in the present pore dimensions after the heat treatment has taken place. This makes it possible, by continuous metered addition of thermoplastic fibers during the formation of the absorbent layer, to continuously increase the fraction of thermoplastic fibers in the direction of the topsheet, which results in a similarly continuous increase in the pore sizes. Thermoplastic fibers can be formed from a multitude of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9000 meters) in diameter may preferably be used. Preferred thermoplastic fibers are from 3 to 50 mm in length, particularly preferred thermoplastic fibers are from 6 to 12 mm in length. The preferred diameter for the thermoplastic fibers is in the range from 1.4 to 10 decitex, and the range from 1.7 to 3.3 decitex (gram per 10 000 meters) is particularly preferred. The form of the fibers may vary; examples include woven types, narrow cylindrical types, cut/split yarn types, staple fiber types and continuous filament fiber types.

The fibers in the absorbent composition of the present invention may be hydrophilic, hydrophobic or a combination of the two. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent, Conversely, a fiber is termed hydrophobic when a contact angle of greater than 90° is formed and no spreading is observed.

Preference is given to using hydrophilic fiber, material. Particular preference is given to using fiber material which is weakly hydrophilic on the body side and at its most hydrophilic in the region surrounding the water-absorbing polymer beads. In the manufacturing process, the use of layers having different hydrophilicities creates a gradient which channels impinging fluid to the hydrogel, where it is ultimately absorbed.

Suitable hydrophilic fibers for use in the absorbent composition of the present invention include for example cellulose fibers, modified cellulose fibers, rayon, polyester fibers, for example polyethylene torophthalate (DACRON®), and hydrophilic nylon (HYDROFIL®). Suitable hydrophilic fibers may also be obtained by hydrophilizing hydrophobic fibers, for example the treatment of thermoplastic fibers obtained from polyolefins (e.g. polyethylene or polypropylene, polyamides, polystyrenes, polyurethanes, etc.) with surfactants or silica. However, for reasons of cost and ease of availability, cellulose fibers are preferred.

The inventive water-absorbing polymer beads are embedded into the fiber material described. This can be done in various ways, for example by using the hydrogel material and the fibers together to create an absorbent layer in the form of a matrix, or by incorporating water-absorbing polymer beads into fiber blend layers, where they are ultimately fixed, whether by means of adhesive or lamination of the layers.

The fluid-acquiring and distributing fiber matrix may comprise synthetic fiber or cellulose fiber or a mix of synthetic fiber and cellulose fiber, in which case the blend ratio may vary from (100 to 0) synthetic fiber: (0 to 100) cellulose fiber. The cellulose fibers used may additionally have been chemically stiffened to increase the dimensional stability of the hygiene article.

The chemical stiffening of cellulose fibers may be provided in different ways. One way of achieving fiber stiffening is by adding suitable coatings to the fiber material. Such additives include, for example, polyamide-epichlorohydrin coatings (Kymene® 557 H, Hercules, Inc. Wilmington, Del., USA), polyacryiamide coatings (described in U.S. Pat. No. 3,556,932 or as the Perez® 631 NC commercial product from American Cyanamid Co., Stamford, Conn. USA), melamine-formaldehyde coatings and polyethyleneimine coatings.

Cellulose fibers can also be chemically stiffened by chemical reaction. For example, suitable crosslinker substances can be added to bring about crosslinking which takes place within the fiber. Suitable crosslinker substances are typical substances which are used to crosslink monomers. They include, but are not limited to, $C_2$-$C_8$-dialdehydes, $C_2$-$C_8$-monoaldehydes having acid functionality and in particular $C_2$-$C_9$-polycarboxylic acids. Specific substances in this group are, for example, glutaraldehyde, glyoxal, glyoxylic acid, formaldehyde and citric add. These substances react with at least two hydroxyl groups within any one cellulose chain or between two adjacent cellulose chains within any one cellulose fiber. The crosslinking stiffens the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. Nos. 3,224,926, 3,440,135, 3,932,209, 4,035,147, 4,822,453, 4,888,093, 4,898,642 and 5,137,537. The chemical crosslinking brings about stiffening of the fiber material, which is ultimately reflected in improved dimensional stability for the hygiene article as a whole. The individual layers are joined together by methods known to the person skilled in the art, for example melting by heat treatment, addition of hot-melt adhesives, latex binders, etc.

Examples of processes to obtain an absorbent composition which comprises, for example, a carrier material which water-absorbing polymer beads are fixed on one or both sides are known and included by the invention but not limited thereto.

Examples of processes to obtain an absorbent composition comprising for example water-absorbing polymer beads (c) embedded into a fiber material blend of synthetic fibers (a) and cellulose fibers (b), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in and (7) a process where (b) and (c) are mixed separately into (a). Of these examples, processes (1) and (5) are preferred. The apparatus used in this process is not particularly restricted and any customary apparatus known to the person skilled in the art can be used. The absorbent composition obtained in this way can optionally be subjected to a heat treatment, so as to result in an absorption layer having excellent dimensional stability in the moist state. The heat treatment process is not particularly restricted. Examples include heat treatment by feeding hot air of the infrared irradiation. The temperature of the heat treatment is in the range from 60° C. to 230° C., preferably from 100° C. to 200° C., particularly preferably from 100° C. to 180° C.

The duration of the heat treatment depends on the type of synthetic fiber, its amount and the hygiene article production rate. Generally the duration of the heat treatment is in the range from 0.5 seconds to 3 minutes, preferably from 1 second to 1 minute.

The absorbent composition generally provided for example with a liquid-pervious topsheet and a liquid impervious backsheet. Furthermore, leg cuffs and adhesive tabs are attached to finalize the hygiene article. The materials and types of pervious topsheet and impervious backsheet and of the leg cuffs and adhesive tabs are known to the person skilled in the art and are not particularly restricted. Examples thereof can be found in WO 95/26209.

The water-absorbing, polymer beads are tested by means of the test methods described below.

Methods

The measurements should, unless stated otherwise, be carried out at an ambient temperature of 23±2° C. and a relative atmospheric humidity of 50±10%. The water-absorbing polymers are mixed thoroughly before the measurement.

Saline Flow Conductivity (SFC)

The saline flow conductivity of a swollen gel layer under pressure load of 0.3 psi (2070 Pa) is, as described in EP-A-0 640 330, determined as the gel layer permeability of a swollen gel layer of superabsorbent polymer, although the apparatus described on page 19 and in FIG. 8 in the aforementioned patent application was modified to the effect that the glass frit (40) is no longer used, the plunger (39) consists of the same polymer material as the cylinder (37) and now comprises 21 bores of equal size distributed uniformly over the entire contact surface. The procedure and the evaluation of the measurement remains unchanged from EP-A-0 640 330. The flow rate is recorded automatically.

The saline flow conductivity (SFC) is calculated as follows:

$$SFC\ [cm^3 s/g] = (Fg(t=0) \times L0)/(d \times A \times WP),$$

where Fg(t=0) is the flow rate of NaCl solution in g/s, which is obtained by means of a linear regression analysis of the Fg(t) data of the flow determinations by extrapolation to t=0, L0 is the thickness of the gel layer in cm, d is the density of the NaCl solution in $g/cm^3$, A is the surface area of the gel layer in $cm^2$ and WP is the hydrostatic pressure over the gel layer in dyn/cm2.

Centrifuge Retention Capacity (CRC)

The centrifuge retention capacity of the water-absorbing polymer beads is determined by the EDANA (European Disposables and Nonwovens Association) recommended test method No. 441.2-02 "Centrifuge Retention Capacity".

The values reported for the centrifuge retention capacity are based on the anhydrous water-absorbing polymer beads, i.e. the values measured were corrected according to the water content of the water-absorbing polymer beads before the measurement. The water content of the water absorbing polymer beads is determined by the EDANA (European Disposables and Nonwovens Association) recommended test method No. 430.2-02 "Moisture content".

The EDANA test methods am obtainable, for example, from the European Disposables and Nonwovens Association. Avenue Eugene Plasky 167, B-1030 Brussels, Belgium.

EXAMPLES 14.6 kg of sodium acrylate (37.5% by weight solution in water) and 1.4 kg of acrylic acid were mixed with 22.4 g of 15-tuply ethoxylated trimethylolpropane triacrylate. The solution was dropletized into a heated dropletization tower filled with nitrogen atmosphere (180° C., height 12 m, width 2 m, gas velocity 0.1 m/s in cocurrent). The metering rate was 16 kg/h. The dropletizer plate had 37 bores of 170 μm. The diameter of the dropletizer plate was 65 mm. The initiator and calcium phosphate were metered individually into the monomer solution via a Venturi mixer just upstream of the dropletizer. The initiator used was a 15% by weight solution of 2,2'-azobis[2-(2-imidazolin-2-yl)propane] dihydrochloride in water. Calcium phosphate was used in the form of a 30% by weight aqueous solution (calcium phosphate dispersion type TCP 130 from Rhodia). The metering rate of the initiator solution was 0.224 kg/h. The gas exit temperature from the dropletization tower was 130° C. The mean particle diameter of the resulting polymer beads was 270 μm.

The resulting water-absorbing polymer beads were then analyzed. The results are summarized in Table 1:

TABLE 1

| Influence of the inorganic salt | | | |
|---|---|---|---|
| Example | Calcium phosphate content*) | CRC [g/g] | SFC [$10^{-7}$ cm$^3$s/g] |
| 1 | none | 41.6 | 1 |
| 2 | 0.5% by wt. | 40.6 | 7 |
| 3 | 3% by wt. | 39.0 | 19 |
| 4 | 5% by wt. | 37.9 | 35 |

*)based on acrylic acid

The invention claimed is:

1. Water-absorbing polymer beads comprising at least partly polymerized ethylenically unsaturated acid-bearing monomers and having a mean sphericity of at least 0.84, a content of hydrophobic solvents of less than 0.005%, by weight, having a centrifuge retention capacity of at least 30 g/g, and a permeability of at least $5 \times 10^{-7}$ to $35 \times 10^{-7}$ cm$^3$ s/g, and which comprise at least 0.5% to 5%, by weight, based on the ethylenically unsaturated acid-bearing monomers, of calcium sulfate or calcium phosphate,
wherein the calcium sulfate or calcium phosphate is added to a solution comprising the ethylenically unsaturated acid monomers used for the polymerization.

2. The water-absorbing polymer beads according to claim 1, having a mean diameter of at least 200 μm.

3. The water-absorbing polymer beads according to claim 1, wherein at least 90%, by weight, of the polymer beads have a diameter of from 100 to 800 μm.

4. The water-absorbing polymer beads according to claim 1, wherein the acid groups of the polymerized monomer are at least partly neutralized.

5. The water-absorbing polymer beads according to claim 1, wherein the ethylenically unsaturated monomer is acrylic acid to an extent of at least 50 mol %.

6. The water-absorbing polymer beads according to claim 1, wherein the water-insoluble salt is calcium phosphate.

* * * * *